United States Patent [19]

Leung

[11] Patent Number: 4,507,121

[45] Date of Patent: Mar. 26, 1985

[54] DISPOSABLE DIAPER WITH ISOLATED WETNESS INDICATOR

[76] Inventor: Martin C. Leung, 656 Scorpio Ln., Foster City, Calif. 94404

[21] Appl. No.: 490,883

[22] Filed: May 2, 1983

[51] Int. Cl.³ .............................................. A61F 13/16
[52] U.S. Cl. ...................................................... 604/361
[58] Field of Search ................. 604/358, 361; 422/56, 422/58

[56] References Cited

U.S. PATENT DOCUMENTS

| | | | |
|---|---|---|---|
| 3,675,654 | 7/1972 | Duncan et al. | 604/361 |
| 3,759,261 | 9/1973 | Wang | 604/361 |
| 3,918,454 | 11/1975 | Korodi | 604/361 |
| 4,287,153 | 9/1981 | Townsend | 604/361 |
| 4,327,731 | 5/1982 | Powell | 604/361 |

*Primary Examiner*—John D. Yasko
*Assistant Examiner*—Christa K. Scott
*Attorney, Agent, or Firm*—Hamrick, Hoffman, Guillot & Kazubowski

[57] ABSTRACT

Wetness indication means for disposable diapers are isolated from the skin of the wearer by unidirectional flow of liquid bodily excretions from absorbing layers of the diaper into an isolated pocket of absorbing materials through a zone containing the chemicals which indicate wetness by changing color.

14 Claims, 5 Drawing Figures

DISPOSABLE DIAPER WITH ISOLATED WETNESS INDICATOR

FIELD OF THE INVENTION

This invention relates to disposable diapers having chemical means for indicating "wetness".

BACKGROUND OF THE INVENTION

In disposable diapers having chemical mechanisms for indicating a wet or dirty diaper, it is desirable to isolate the chemicals of the mechanism from contact with skin of the wearer. In particular, skin sensitivity to such chemicals cannot reliably be predicted. Also, many water-soluble or disperable color change indicating substances thought to be benign may actually have toxic consequences related to the chemical environment within a wet diaper and/or the frequency of contact with the chemical substances. Also, frequent exposure to certain chemicals, and particularly those which change color responsive to changes in the Ph can stimulate allergy reactions, particularly in circumstances where there is repeated exposure. Even in those instances where the chemical indicating agents are expressly insoluble in water, care must be taken to preclude, for example, free ions which induce the color change from contacting the skin's surface. (See U.S. Pat. No. 4,287,153, N. S. Townsend, entitled "Disposable Article With Non-Leachable Saline Water Indicator".) Finally, mothers simply will not accept any diaper with a wetness indicator where there is the remotest possibiliy of the skin becoming stained.

SUMMARY OF THE INVENTION

A disposable diaper is described wherein a chemical color change wetness indicator is isolated from contacting the skin of the wearer by a capillary structure which induces flow of liquids from the absorbing materials of the diaper into an isolated pocket of liquid-absorbing materials through a zone containing a chemical wetness indicator. Specifically, in the described diaper of the chemicals of the wetness indicator are isolated from the liquids within the diaper except through capillary channels connecting an isolated pocket of absorbing materials with the remainder of the diaper.

Other features of the disposable diaper relate to adjusting the capacity of the absorbing materials within the isolated pocket for absorbing liquids in order to insure unidirectional flow of liquids through the capillary structure over an extended time interval, and to construction of the isolated pocket and configuration of the absorbing material located therein.

The advantages of a disposable diaper with the described construction relate to the unidirectional flow of the liquid bodily excretions which leaches all free or soluble chemical agents of the indicating means into the isolated pocket, thus preventing diffusion of such chemical agents through the absorbing materials of the diaper into contact with the skin of the wearer. Still other features, aspects and advantages of the invented diaper and illustrative embodiments thereof are more fully described with reference to the following description and drawings.

DESCRIPTION OF PREFERRED AND ILLUSTRATIVE EMBODIMENTS

Figure 1:
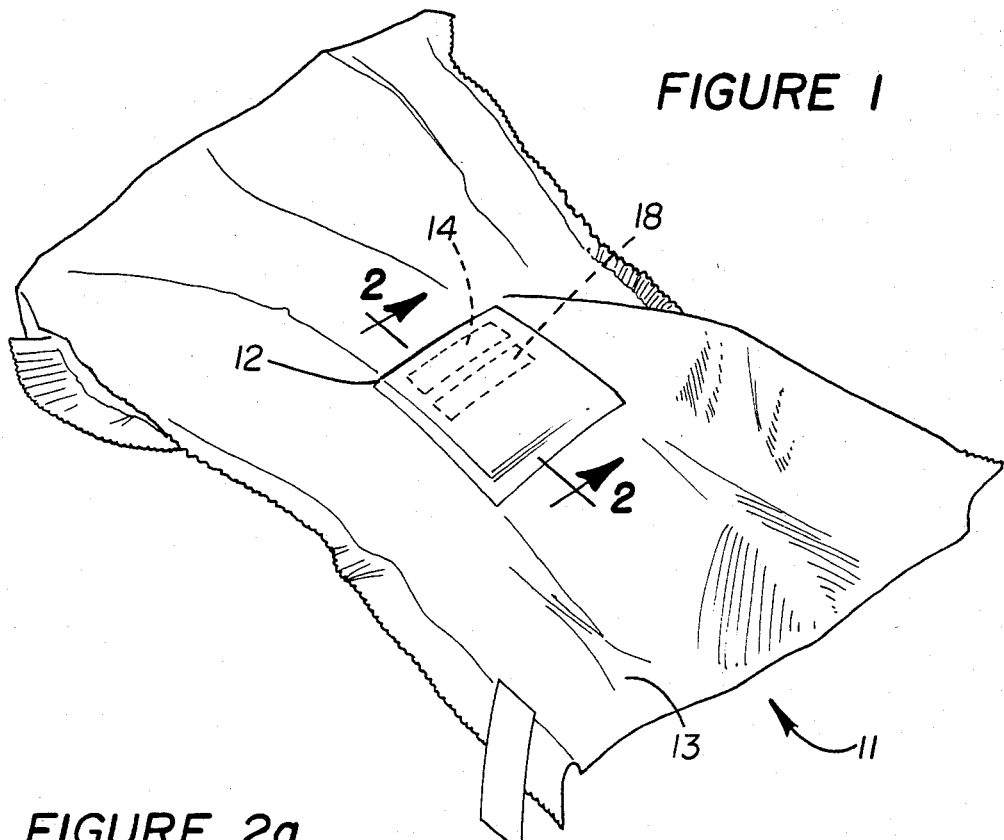
FIG. 1 is a perspective view of the backside of a disposable diaper illustrating a possible location for the isolated pocket of absorbing material on the exterior of the water-impermeable backsheet of the diaper.

Referring to FIG. 1, the backside of a conventional disposable diaper 11, is shown. An exterior pocket 12 is secured to the exterior surface of the water-impermeable backsheet 13 in an area that would normally be visible from the back when the diaper is worn by an infant.

A rectangular opening 14 is cut through the backsheet 13 establishing a liquid communication channel between the absorbing materials 16 within the diaper and the absorbing materials 17 within the exterior pocket.

Figure 2A:
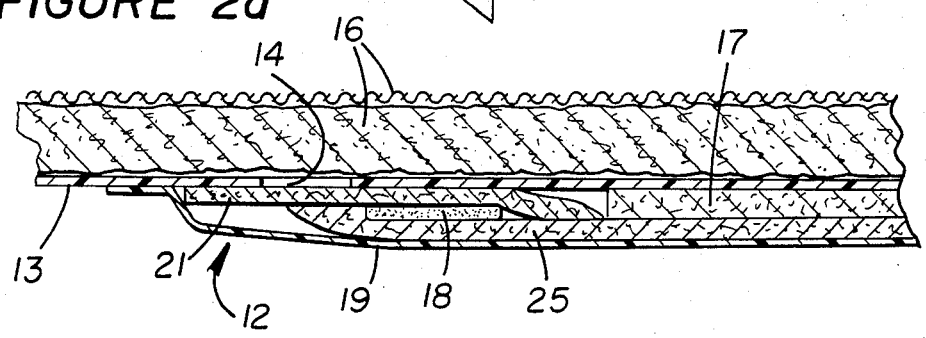
FIG. 2(a) shows a cross-sectional view of the disposable diaper taken along Line 2—2 of FIG. 1.
Figure 3:
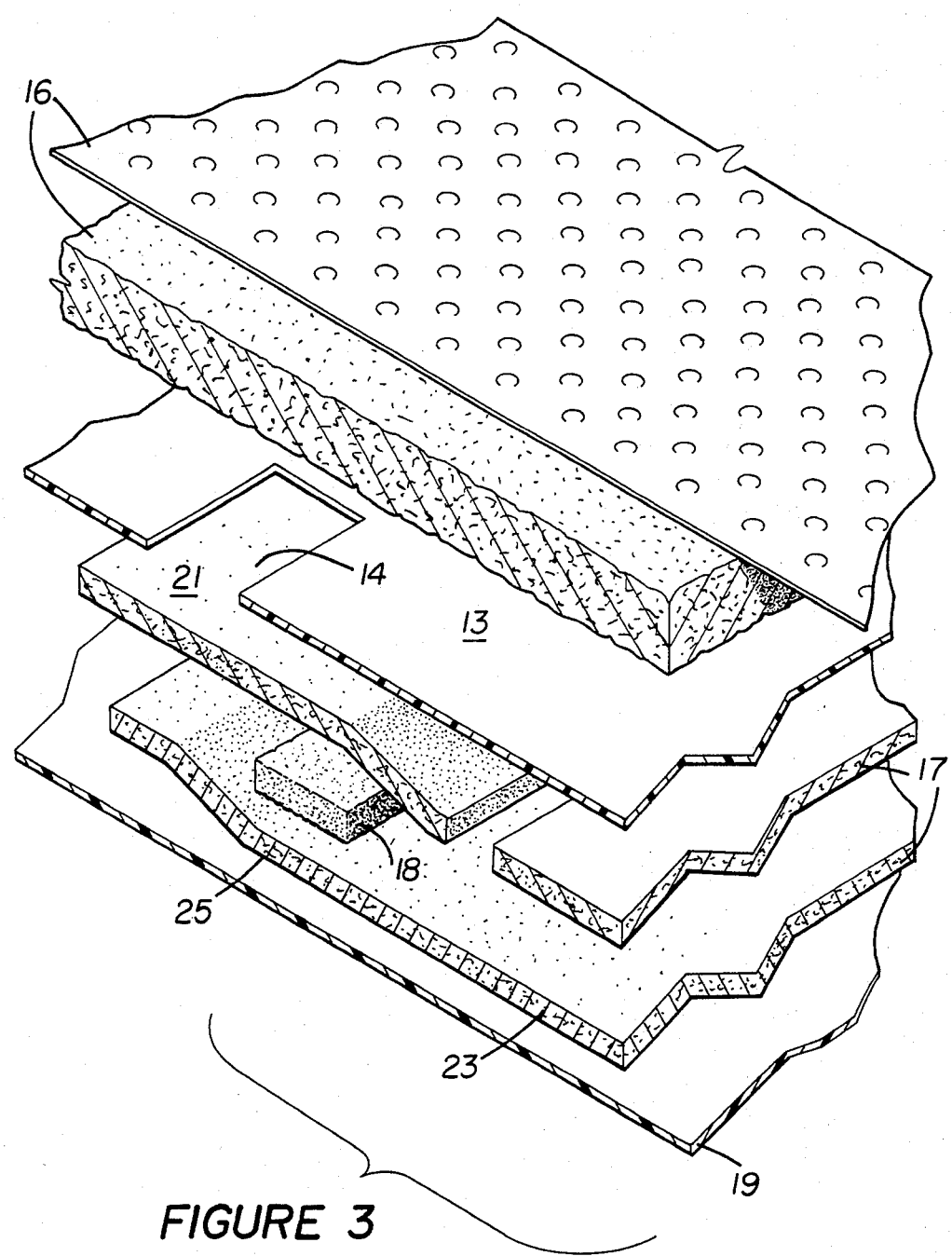
FIG. 3 is an exploded cross-sectional view of the invented disposable diaper illustrating the relationship of the materials.

As is more clearly illustrated in FIGS. 2(a) and 3, adjacent the opening 14 through the backsheet 13 is a strip of wicking material 18 treated with suitable chemicals for indicating the presence of moisture or wetness with a color response. In more detail, the exterior pocket 12 is formed by bonding a water-impermeable sheet 19 to the exterior surface of the backsheet 13. The impermeable sheet 19 should be transparent or translucent such that the color response of the chemical indicating means within the wicking material 18 can be visually perceived. The strip of chemically treated wicking material 18 should be placed proximate, but not over, the hole 14. Untreated wicking materials 21 of the same type of material as the remainder of the liquid-absorbing materials 17 were placed over the opening 14. As illustrated in FIGS. 2(a) and 3, the chemically treated strip of wicking material 18 is sandwiched between the wicking material 21, which extends over the opening 14 and a sheet of wicking material 25 which extends into and is integral with the liquid absorbing materials 17 which fill the remainder of the pocket 12.

The liquid excretions of an infant are conventionally absorbed by the liquid-absorbing materials 16 within the diaper 11. The opening 14 through the backsheet 13 affords liquid communication between the absorbing material 16 and the wicking material placed over the opening 14. The capillary structure of the wicking material 21 draws the liquid from the absorbing material 16 into contact with the chemically treated strip 18 of wicking material whereupon the chemicals react, giving a color response. The capillary structure of the strip 18 then conveys the liquid into contact with the liquid-absorbing materials 17 within the remainder of the pocket.

The distance between the chemically treated strip 18 of wicking material and the opening 14 should be greater than the diffusion distance of the chemicals providing the color response against the unidirectional flow of liquid through the capillary structure of the wicking material 21. There should also be a sufficient amount of liquid-absorbing materials 17 to absorb all of the liquid transported into the pocket 12 by the capillary structure of the wicking material 21 for a time interval of at least several hours.

In circumstances where longer time intervals are desired, the wicking material may be composed of a material which expands or swells upon exposure to moisture to effectively close off the capillary channels through which the liquids flow. The expansion of the wicking materials 21 decreases the flow of liquid excretions into the isolated pocket 12 as a function of time and effectively precludes flow of liquids from the absorbing materials 17 within the pocket 12 back into the diaper 11.

Figure 2B:
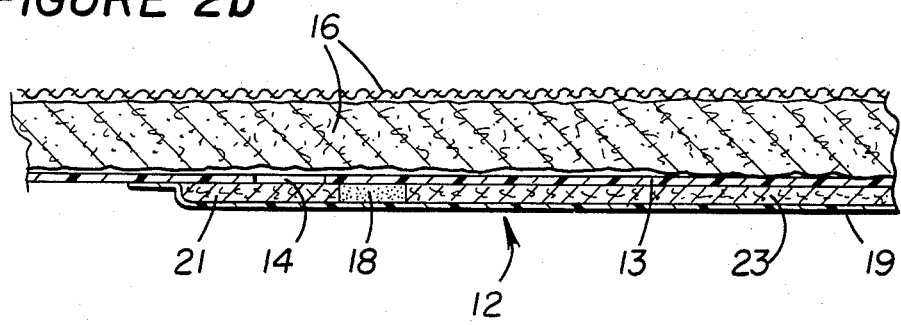
FIG. 2(b) is a cross-sectional view taken along view 2—2 of FIG. 1 of a disposable diaper showing a different configuration of materials within the isolated pocket.

FIG. 2(b) illustrates an alternative arrangement for materials within the isolated pocket. Specifically, the chemical indicating agents are impregnated or deposited directly into a zone 18 of the absorbing materials within a pocket 12. In this case, the absorbing materials may also have zones of different composition. For example, the zone 21 of the absorbing materials covering the opening 14 may be principally composed of a wicking material whereas the materials 23 beyond the chemically impregnated zone 18 may be principally composed of liquid absorption materials.

In order to insure that flow of liquids into the isolated pocket 12 is unidirectional, it is desirable to select or arrange materials in the strip or zone 18 such that they absorb liquids from the wicking material 21 over the hole 14 at a rate greater than that the wicking material 21 absorbs liquids from the absorbing materials 16 within the diaper. Similarly, the absorbing materials 17/23 should be selected or arranged for absorbing liquids from the chemically impregnated zone or strip 18 at a rate greater than that which the zone or strip 18 absorbs liquids from the wicking material 21. A mechanism for accomplishing such a result is illustrated in FIG. 4.

Figure 4:
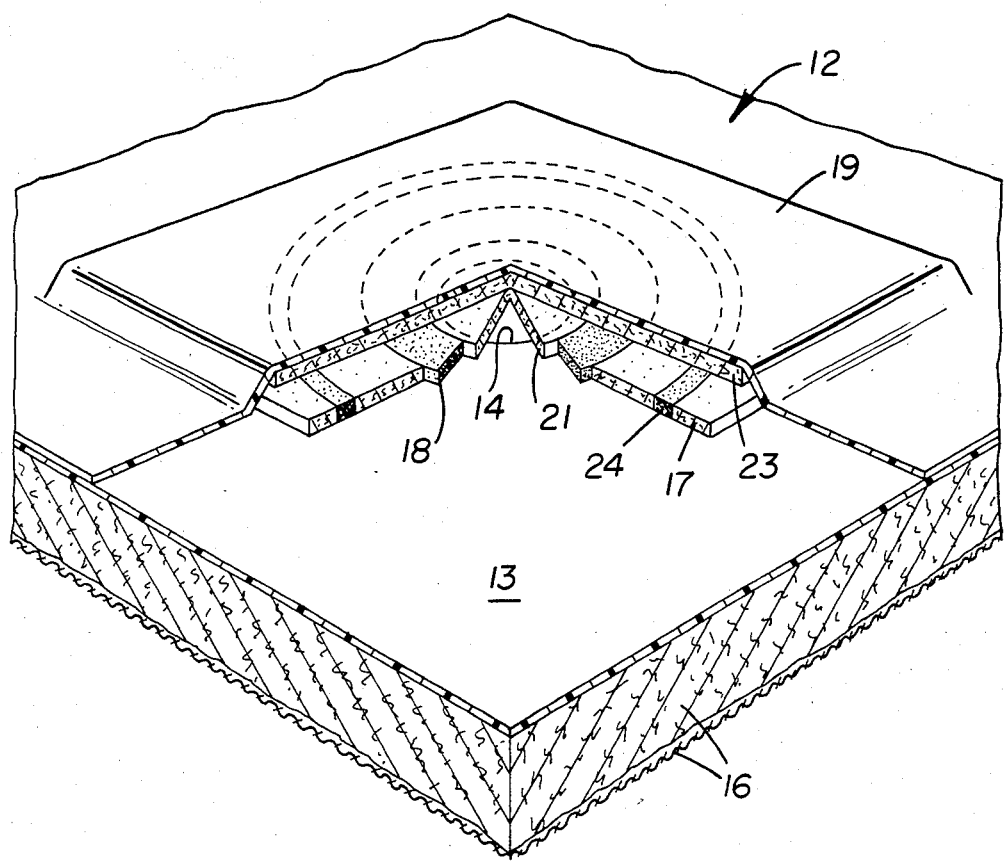
FIG. 4 is a perspective view of the backside of a disposable diaper illustrating an alternative configuration of materials in the isolated pocket.

In particular, shown in FIG. 4 is a top view of the isolated pocket 12 again secured to the exterior face of the backsheet 13 of the diaper. In this embodiment, the opening 14 is a circular orifice through the backsheet 13. A circular disk of wicking material 21 is placed over the orifice 14 which, in turn, is surrounded by an annular zone 18 impregnated with chemical indicator agents. The chemically impregnated zone 18 is in turn surrounded by the remainder of the absorbing materials 17/23 within the pocket 12. In the illustrated arrangement, the zone 18 impregnated with chemical indicating agents would have the capacity to absorb liquids from the zone 21 at a rate greater than that the disk of wicking material 21 zone absorb liquids through the orifice 14 since the absorbing area of the zone 18 would be greater than that of the wicking material 21 over the opening 14. Similarly, the absorbing area of the zone 23 behind the indicator zone 18 would have a greater absorbing area than that of the indicator zone 18.

Also illustrated in FIG. 4 is a second anular zone 24 within the pocket 12 which is also impregnated with chemical indicator agents. This second anular zone 24 functions as a signal warning that the absorbing materials within the isolated pocket 12 are near capacity.

There are numerous chemical agents described in the literature which are suitable for signaling the presence of moisture or wetness in diapers with a color change. Examples of such chemicals and the mechanism of particular chemical reactions signalling the presence of moisture or wetness are described in U.S. Pat. No. 4,327,731 issued to N. B. Powell; No. 4,287,153 issued to M. S. Townsend; No. 4,231,370, issued to J. C. Morz, et al.; and No. 3,675,654, issued to J. S. Baker, et al.

While the invented disposable diaper is described with respect to particular representative embodiments, it should be apparant that changes and variations can be made to such embodiments which will still fall within the scope of the invention as defined in the following claims:

I claim:

1. In a disposable diaper having an inner layer of materials for absorbing bodily excretions and a water-impermeable backsheet retaining the inner layer of absorbing materials and bodily excretions absorbed thereby, the combination comprising,
   - a first layer of moisture-wicking material located on the exterior surface of the backsheet,
   - an opening through the water-impermeable backsheet for providing liquid communication between the inner layer of absorbing materials and the first layer of moisture-wicking material,
   - a strip of moisture-wicking material impregnated with moisture-indicating materials for absorbing liquid from the first layer of moisture-wicking materials,
   - a third layer of moisture-wicking material for absorbing liquid from the strip of moisture-wicking materials impregnated with moisture-indicating materials for providing unidirectional flow of liquid components of the bodily excretions from the opening through the backsheet into the third layer of moisture-wicking materials through the strip of moisture-wicking materials impregnated with moisture-indicating materials,
   - a semi-transparent, water-impermeable sheet covering first, and third layers and the strip of wicking materials, and
   - means securing the semi-transparent sheet to the backsheet to provide an isolated pocket securing the first and third layers and the strip of wicking materials in position over the opening through the backsheet.

2. The disposable diaper of claim 1, wherein the strip of wicking material impregnated with moisture-indicating materials absorbs liquids at a rate greater than the first layer of wicking material and the third layer of wicking materials absorbs liquids at a rate greater than the strip of wicking materials.

3. The disposable diaper of claim 1, wherein the first layer of wicking materials has a capillary structure for establishing a pressure gradient inducing liquid flow to the strip of wicking material and the third layer of wicking material has a capillary structure establishing a pressure gradient inducing liquid flow away from the strip of wicking material.

4. The disposable diaper of claim 1, wherein the strip of wicking material is located proximate the opening through the backsheet.

5. The disposable diaper of claim 1, wherein the first layer of wicking material absorbs liquids at a particular rate and the third layer of wicking material has a capacity for absorbing such liquids for a specific period of time after liquids of the bodily excretions pass through the opening in the backsheet.

6. The disposable diaper of claim 5, wherein the material composing the first layer of wicking materials has the property of swelling on contact with such liquids for decreasing the wicking action of the layer as a function of time.

7. In a disposable diaper including an inner layer of materials for absorbing bodily liquid excretions and a liquid-impermeable backsheet retaining the inner layer of absorbing materials and both absorbed and unabsorbed excretions, the combination comprising, means for providing a pocket in combination with the water-impermeable backsheet isolated from the inner layer of absorbing materials by a liquid-impermeable barrier, means for establishing undirectional liquid flow from the inner layer of absorbing materials into the pocket, means located within the pocket for placing a substance which provides a visual response to the presence of moisture in the unidirectional flow of liquid into the pocket, the pocket being sufficiently transparent to allow visual perception of the response of the substance visually responding to the presence of moisture.

8. The disposable diaper of claim 7, wherein the means for establishing unidirectional liquid flow from the inner layer of absorbing materials into the pocket includes an opening into the pocket for establishing liquid communication into the pocket, a first zone of liquid-absorbing and wicking material covering the opening, a second zone of liquid-absorbing and wicking material surrounding said first zone, and a third zone of liquid-absorbing and wicking material surrounding the second zone.

9. The disposable diaper of claim 7, wherein the means for introducing a substance which visually indicates the presence of moisture into the unidirectional flow of liquids within the pocket comprises chemical indicators for changing color responsive to the presence of moisture located within the second zone of liquid-absorbing and wicking materials within the pocket.

10. The disposable diaper of claim 9, wherein the chemical agents indicating the presence of moisture are leachable from the second zone of liquid-absorbing and wicking materials.

11. A disposable diaper of claim 9, wherein the chemical substance visually indicating the presence of moisture is insoluble in liquids composed of bodily secretions.

12. The disposable diaper of claim 8, wherein a fourth zone of liquid-absorbing and wicking material surrounds the third zone and a substance which visually indicates the presence of moisture is located within such fourth zone to provide a visual indication that the liquid-absorbing and wicking materials within the pocket are approaching capacity.

13. The disposable diaper of claim 8, wherein the first zone of liquid-absorbing and wicking materials absorbs liquids at a rate and the third zone of liquid absorbing and wicking material has a capacity to absorb liquids adjusted to the rate of liquid absorption of the first zone for providing a long interval of time before the capacity of the third zone is reached.

14. The disposable diaper of claim 13, wherein the first zone of liquid-absorbing and wicking material includes a material which has a property of swelling on contact with liquids, decreasing the rate at which such zone absorbs liquids as a function of time.

* * * * *